United States Patent [19]

Nakamura

[11] Patent Number: 5,711,604
[45] Date of Patent: Jan. 27, 1998

[54] METHOD FOR MEASURING THE COEFFICIENT OF HEAT CONDUCTIVITY OF A SAMPLE

[75] Inventor: Nobutaka Nakamura, Chiba, Japan

[73] Assignee: Seiko Instruments Inc., Chiba, Japan

[21] Appl. No.: 552,548

[22] Filed: Nov. 3, 1995

Related U.S. Application Data

[63] Continuation-in-part of Ser. No. 355,720, Dec. 14, 1994, abandoned.

[30] Foreign Application Priority Data

Dec. 14, 1993 [JP] Japan ................... 5-313671

[51] Int. Cl.$^6$ ................... G01N 25/18; G01N 25/00
[52] U.S. Cl. ................... 374/44; 374/12; 374/10
[58] Field of Search ................... 374/44, 10, 12, 374/16, 31, 11

[56] References Cited

U.S. PATENT DOCUMENTS

| | | | |
|---|---|---|---|
| 5,099,441 | 3/1992 | Mazzio | 374/44 |
| 5,112,136 | 5/1992 | Sakuma et al. | 374/44 |
| 5,159,569 | 10/1992 | Xu et al. | 374/45 |
| 5,163,753 | 11/1992 | Whiting et al. | 374/10 |
| 5,257,532 | 11/1993 | Hayakawa et al. | 374/45 |
| 5,288,147 | 2/1994 | Schaefer et al. | 374/10 |
| 5,335,993 | 8/1994 | Marcus et al. | 374/44 |
| 5,599,104 | 2/1997 | Nakamura et al. | 374/12 |

FOREIGN PATENT DOCUMENTS

| | | |
|---|---|---|
| 4-79535 | 3/1981 | Japan. |
| 3-156351 | 2/1983 | Japan. |

*Primary Examiner*—Diego F. F. Gutierrez
*Attorney, Agent, or Firm*—Loeb & Loeb LLP

[57] ABSTRACT

A method for measuring the coefficient of thermal conductivity of a solid sample material by: heating a meltable calibration sample having good thermal conductivity to its melting temperature by raising the temperature of an analyzer at a controlled rate and causing heat to flow through a path having a thermal resistance to the calibration sample, the heating being performed one time with the solid sample material interposed in the path so that heat flows through the path and through the solid sample material, and one time with the solid sample material removed so that heat flows only through the path; deriving thermal analysis curves each representing a relation between heat flow to the calibration sample and the controlled rate at which the analyzer temperature is raised, during melting of the calibration sample in respective performances of the heating step; and determining the coefficient of thermal conductivity of the solid sample material based on the solid sample material thickness and a characteristic of the thermal analysis curves at the melting temperature of the calibration sample.

6 Claims, 2 Drawing Sheets

METHOD FOR MEASURING THE COEFFICIENT OF HEAT CONDUCTIVITY OF A SAMPLE

CROSS-REFERENCE TO RELATED APPLICATION

The present application is a continuation-in-part of application Ser. No. 08/355,720 filed Dec. 14, 1994, now abandoned, the entirety of which is incorporated herein by reference.

BACKGROUND OF THE INVENTION

The present invention relates to a method for observing the change in physical characteristics of materials in relation to temperature or time, using a known thermal analyzer. The invention relates more particularly to measurement of the coefficient of thermal conductivity of materials using a known differential scanning calorimeter.

The coefficient of thermal conductivity of a material is an important parameter in material analysis. It is one of the three constants which determine the thermal characteristics of materials, together with thermal diffusibility and specific heat. The following relation exists among those three constants of isotropic materials:

thermal diffusibility×specific heat×density=coefficient of thermal conductivity

Once two of those constants are known, together with the density of a material, the third constant can be determined on the basis of the above equation.

It is also known, as disclosed in, for example, JIS K 7123 Testing Methods for Specific Heat Capacity for Plastics, that the specific heat of plastic materials can be measured using a differential scanning calorimeter (DSC). Therefore, once a coefficient of the thermal conductivity or thermal diffusibility of a material is determined with a DSC, all three thermal constants can be determined by use of the DSC. This offers a substantial engineering advantage.

The heat capacity of solid materials can only vary within a range of several orders of magnitude, independent of the type of material. On the other hand, the coefficient of thermal conductivity and thermal diffusibility of such materials varies over a range of two to four orders of magnitude as between metals and polymer materials. In addition, the values of these parameters vary considerably between different polymer materials. Since these differences relate directly to heat radiation characteristics of materials, measurement of the coefficient of thermal conductivity and thermal diffusibility is of great importance, from the industrial point of view, in the field of material testing.

The following methods for determining the coefficient of thermal conductivity and thermal diffusibility of materials are known in the art:

a) Alternating current thermal response analysis.

While an alternating current heat flow is supplied to one side of a thin film sample, the frequency or phase of variation of the resulting temperature, detected by a temperature sensor fixed to the sample, is compared with the frequency or phase of alternating current heat flows for obtaining an indication of thermal diffusibility. This method is called alternating calorimetry and is disclosed in Japanese Patent Publications Tokkohei 04-79535 and Tokkaihei 03-156351.

b) Transient pulse thermal response analysis.

While a heat pulse is supplied to one side of a thin film sample using a laser, etc., the coefficient of thermal conductivity of the sample can be determined by analyzing the change in temperature at the other side of the sample. This is known as laser flash calorimetry.

c) Direct current thermal response analysis.

While a definite heat flow is supplied to one side of a thin film sample, the coefficient of thermal conductivity of the sample can be determined by measuring the temperature differential between the two sides of the sample and comparing the ratio of the magnitude of the heat flow to the temperature differential.

Chiu et al., in Thermochimical Acta, 34, pp. 267–273 (1979), disclose modifying a DSC in order to measure the surface temperature of a sample, and measure the coefficient of thermal conductivity of the sample, according to a variation of the direct current thermal response analysis method.

DSCs are among the most widely used calorimeters and are used for measuring the transition temperatures at a melting point, crystallization point, glass transition point, etc., of sample materials. This subject matter is disclosed in JIS K No. 7121 and JIS H No. 7101. In addition, DSCs are used in fields of physical chemistry analysis such as for measurement of transition heat or radiation heat, or measurement of specific heat, as described in JIS K No. 7123. At the time of calibration of a DSC output temperature, there is employed a procedure which involves difference compensation between the transition temperatures occurring in an empty container and in a container provided with a known sample of a high purity metal having a known transition temperature, under the influence of a constant programming rate of heating. The behavior of the resulting DSC curve as the temperature passes through the melting point of the pure metal, with respect to time, is represented by curve 10 in FIG. 2. The maximum negative gradient of the curve is proportional to the programming rate of heating and inversely proportional to the thermal resistance between the sample and the heater.

In the prior art procedures, it is necessary to provide special apparatus exclusively for the measurement of coefficient of thermal conductivity. On the one hand, in the case of methods a) and b), above, it is necessary to provide a thin film sample and to perform a special preliminary treatment such as deposition of a metal foil or attachment of a thermocouple using silver paste to fix the temperature sensor to the sample. On the other hand, method c) also has not been widely adopted because it requires modification of the DSC to add a structure for measuring the temperature of the sample upper surface.

SUMMARY OF THE INVENTION

In order to solve the above-described problems in the prior art, a temperature calibration method used in existing thermal analyzers is employed and measurement of a high purity sample is made after forming a one-dimensional heat flow path through an unknown sample material and between a temperature sensor and a sample container. Specifically, at a sample station of a thermal analyzer for measuring flows of heat into and out of a sample as a function of time or temperature, such as a DSC, a plate-shaped unknown sample to be measured, having a known thickness and known surface area, and a calibration sample constituted by a high purity metal for temperature calibration are enclosed in a container made of a material having good thermal conductivity and having a bottom area of known size. Then, measurements are performed under control of a programmed constant rate of temperature in order to determine the coefficient of thermal conductivity of the unknown sample. In particular, the peak wave of the DSC curve is analyzed by the above-described measurement in comparison to the curve obtained when the sample is not present.

The reciprocal of the largest absolute gradient value around the peak of the DSC curve, corresponding to the melting point of the calibration sample, is proportional to the thermal resistance between the calibration sample and the heater. Therefore, by obtaining the difference between the reciprocal of the maximum gradient of the DSC curve with and without the unknown sample present, the incremental value of thermal resistance provided by the measured sample can be determined. Then, by multiplying the programmed rate of temperature by the above-mentioned difference and by the surface area of the container, and then dividing the thickness of the unknown sample material by the product of that multiplication, the value of the coefficient of thermal conductivity of the unknown sample can finally be obtained.

DESCRIPTION OF THE PREFERRED EMBODIMENTS

Based on the illustrations shown in FIGS. 1 and 2, the present invention will be described in greater detail below.

Figure 1:
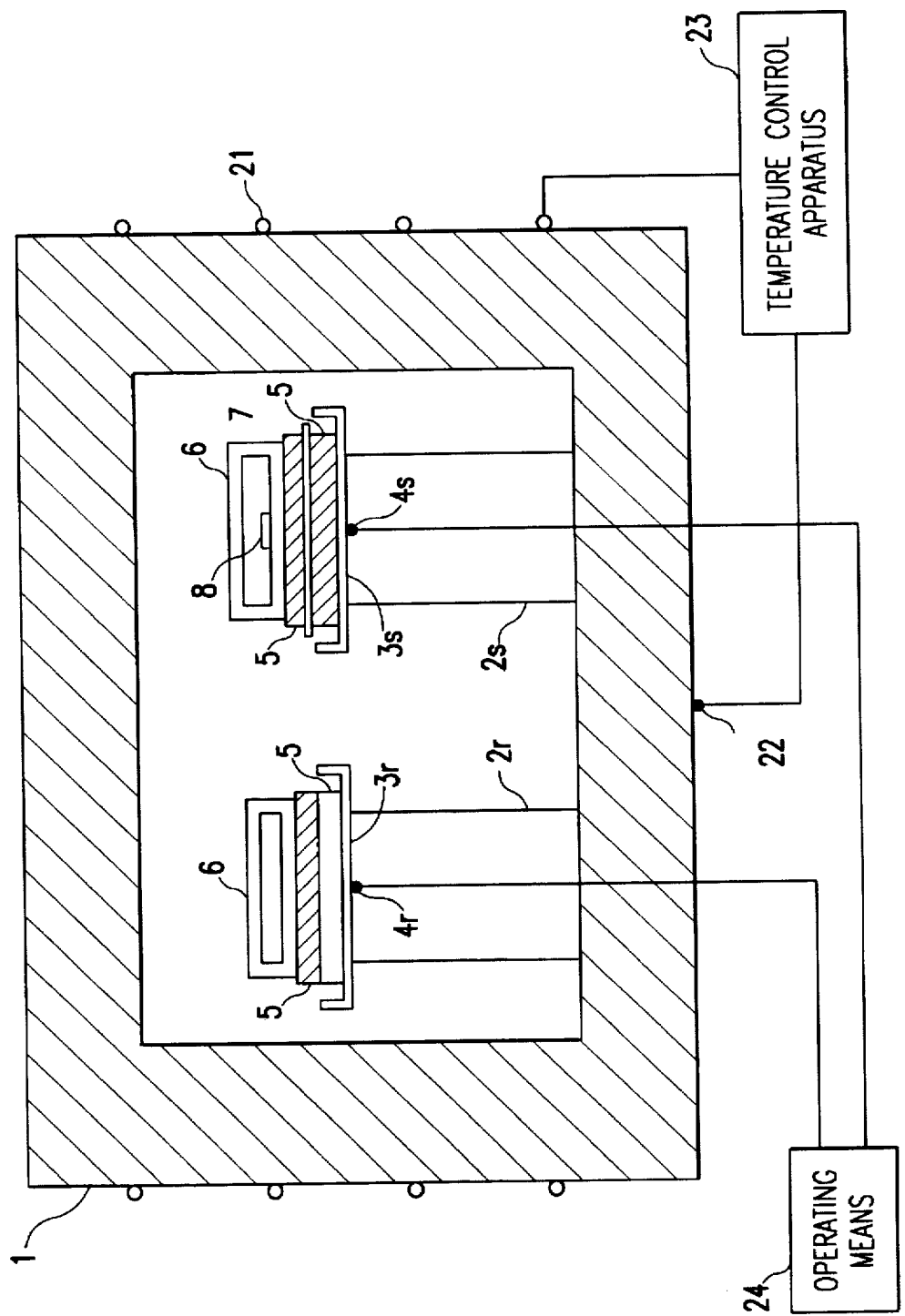
FIG. 1 is a cross-sectional view of an apparatus employed for performing measurements in accordance with the present invention.

FIG. 1 shows the basic components of a DSC, including a heat sink 1 made of silver or other material having a good thermal conductivity. Sink 1 is made of a material having a good thermal conductivity in order to obtain a homogeneous temperature within the sink. A sample holder 3s and a reference holder 3r are mounted within sink 1. Holders 3s and 3r are identical to one another and are symmetrically positioned relative to one another in sink 1. Holders 3s and 3r are supported in sink 1 by respective elements 2s and 2r having identical thermal resistances. Element 2s provides a sample side thermal resistance, and element 2r provides a reference side thermal resistance. At the bottom of sample holder 3s and reference holder 3r, there are mounted a temperature sensor 4s and a temperature sensor 4r, respectively, for measuring the temperatures of sample holder 3s and reference holder 3r. Two silver discs 5 are placed on each holder 3r and 3s and a respective sample container 6 is place on each pair of discs 5.

Each container 6 may be made of a high purity metal having a high coefficient of thermal conductivity, such as aluminum, silver, stainless steel, etc.

On sample holder 3s, a disc-shaped sample 7 to be measured is placed between silver discs 5. Sample 7 has a larger diameter than each disc 5. A high purity indium body 8 is provided in the container 6 which is mounted on sample holder 3s.

A heater 21 is coiled around the outside of heat sink 1 and is provided for the purpose of heating heat sink 1. Heater 21 is connected to a temperature control apparatus 23 for supplying electric power in order to vary the temperature within heat sink 1 according to a predetermined temperature program. The operation of temperature control apparatus 23 is controlled in response to the output of a temperature sensor 22 fixed to heat sink 1. Temperature sensor 22 supplies a signal representing the temperature of heat sink 1 to apparatus 23. The apparatus shown in FIG. 1 and described above will be referred to hereinafter as DSC apparatus.

For performing a first measurement, components are disposed in heat sink 1, as illustrated in FIG. 1. Then, in accordance with a selected temperature control program, which may involve a linear increase in the temperature of heat sink 1, heater 21 is operated to effect heating of heat sink 1. During this heating, signals representing the temperatures measured by sensors 4r and 4s are supplied to an operating means 24, where the difference between those temperatures is recorded as a function of time or the temperature measured by sensor 22 or 4r.

Two measuring procedures are performed in the DSC. In one of these procedures, a sample 7 to be measured is provided between the two silver discs 5 on sample holder 3s and temperature apparatus 23 is operated to increase the temperature of sink 1 at a constant rate, the temperature passing through the value at which indium body 8 will melt. The differential temperature value applied to operating means 24 varies as a function of time as represented by the solid line curve 10 in FIG. 2. The same operation is performed, but with no sample 7 present on holder 3s. The resulting variation of the difference in temperature values applied to operating means 24 with respect to time is represented by the broken line curve 11 in FIG. 2.

In operating means 24, the maximum absolute values for the slope of each of curves 10 and 11 at the location associated with the melting point of indium body 8 are calculated, based on the stored data for curves 10 and 11. The product of the programmed rate (B) of temperature change, or rate of heating and the surface area (A) of a disc 5, or of the bottom of holder 3s if no disc 5 is employed, is obtained. Then the product of the thickness (t) of sample 7 and the reciprocal of AB is obtained. That product is then multiplied by a term which is equal to the difference between the reciprocals of the maximum gradients of curves 10 and 11 to obtain the value of the coefficient of thermal conductivity of sample 7. Thus, operating means 24 calculates the largest absolute values for the slopes of curves 10 and 11, which maximum slope values are the slopes of lines 10s and 11s in FIG. 2.

The meaning of the calculations described above will now be explained. The DSC output signal, which is the difference between the output signal of sensor 4r and the output signal of sensor 4s, is substantially constant with respect to time up to the vicinity of the melting point of indium body 8. This is because both sensor outputs have stable, or linear, temperature characteristics in that temperature range. In addition, since most of the thermal energy conducted from sink 1 toward body 8 via element 2s is absorbed by indium body 8 as latent heat at the melting temperature of body 8, the DSC signal has a large absolute value. This means that heat flowing to sample holder 3s is absorbed as heat of fusion of indium body 8 so that its temperature does not continue to rise while the temperature of reference holder 4r continues to increase at a constant rate, so that the difference between the temperatures increases. As melting of the indium body is completed, the DSC signal gradually returns to its original value, which it had before indium body 8 was brought to its temperature. Curves 10 and 11 shown in FIG. 2 can be considered to represent the variation of the temperature indicated by sensor 4s minus the temperature indicated by temperature sensor 4r.

Figure 2:
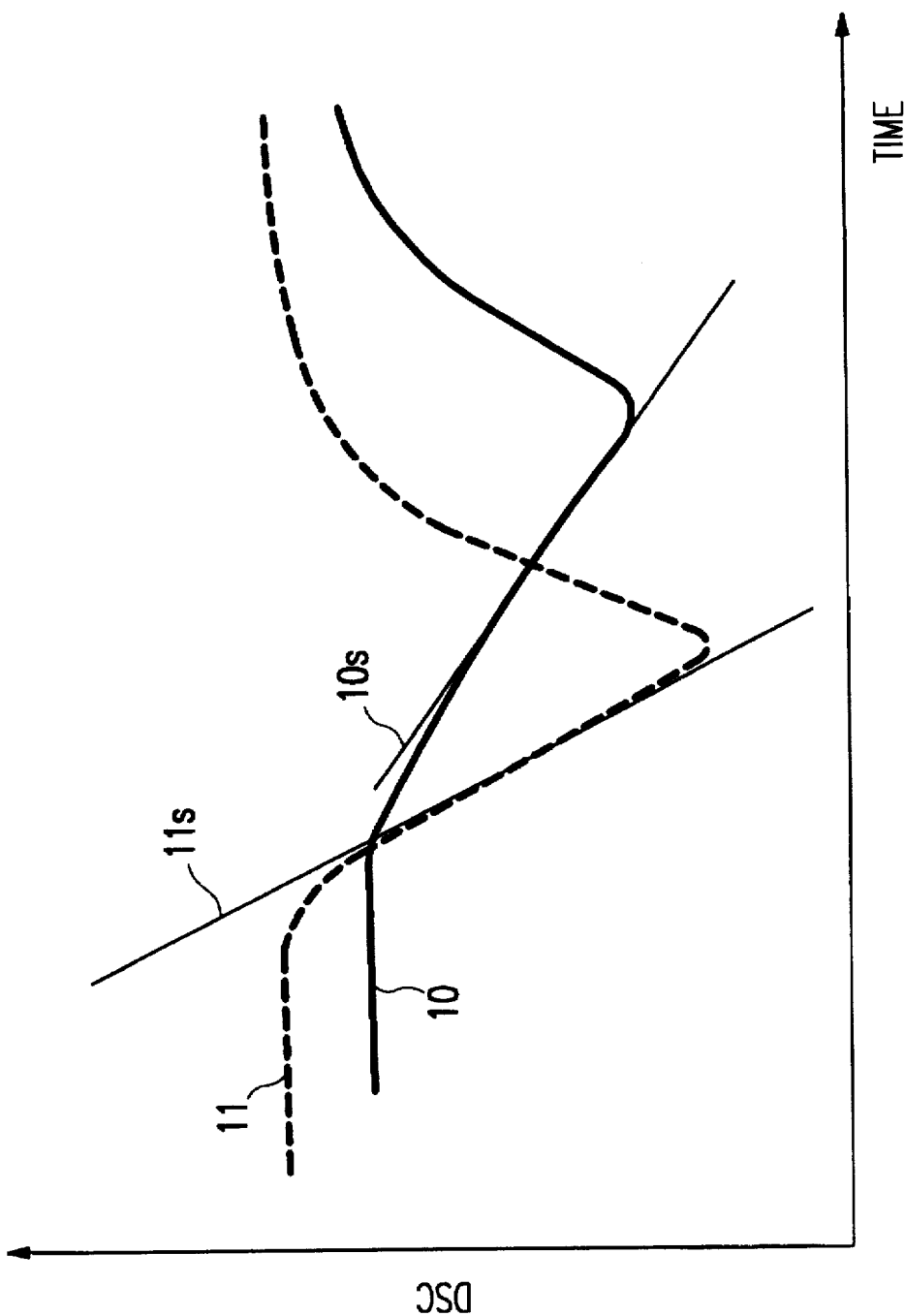
FIG. 2 is a graph showing thermal analysis curves obtained during the course of measurements according to the invention.

As noted above, the variation in the DSC signal with respect to time in the vicinity of the melting temperature of a high purity indium body 8, when a sample 7 is present on holder 3s, is represented by the solid line curve 10 in FIG. 2.

Now, the situation where no sample 7 is present on holder 3s will be explained. In this case, only the two silver discs 5 and sample container 6 containing indium body 8 are present on holder 3s. When there is no sample 7 present, the variation of the DSC output signal at the time is represented by broken line 11 in FIG. 2. As noted above, the data for both curves 10 and 11 are stored in operating means 24.

The difference between curves 10 and 11 originates in the difference in heat flow path from the tops of both elements 3s and 3r to the respective sample containers 6, the difference being due to the presence of sample 7 on holder 3s, while a body corresponding to sample 7 is not present on holder 3r. The thermal resistance difference between the two paths is equal to the thermal resistance of sample 7.

The straight lines 10s and 11s represent the tangents to curves 10 and 11 at the location where their slopes have the maximum absolute values. The absolute values of the slopes of lines 10s and 11s are P and Q, respectively.

Q is thus the absolute value of the rate of change of the DSC signal at the melting point of indium when there is no sample 7 present on holder 3s:

$$Q = B/R_o,$$

where Ro is the thermal resistance from heat sink 1 to indium body 8 when there is no sample 7 on holder 3s.

Similarly, P is the absolute value of the rate of change of the DSC signal at the melting point of indium when a sample 7 is present on holder 3s, and particularly between silver discs 5:

$$P = B/R_s,$$

where Rs is the thermal resistance from heat sink 1 to indium body 8 when a sample 7 is present on sample holder 3s.

The thermal resistance R of sample 7 is:

$$R = t/Ak,$$

where t is the thickness of sample 7, in the direction between discs 5;

A is the surface area of the bottom of a silver disc 5, or the surface area of the bottom of sample container 3s when no silver discs are provided, and k is the coefficient of thermal conductivity of sample 7. In addition:

$$R_s = R_o + R.$$

From the above equations, the following relation can be developed:

$$k = \frac{t}{A \cdot B \cdot \left(\frac{1}{P} - \frac{1}{Q}\right)}$$

where B is the programmed rate of temperature change produced by temperature control apparatus 23, B preferably being a constant.

In the calculation of P and Q values, the DSC signal may be one which varies with respect to time or temperature, particularly when B is a constant. In addition, the method according to the invention can be carried out without utilizing silver discs 5, particularly if there is no concern about whether sample 7 will contaminate sample holder 3s when in direct contact therewith, or that the temperature at any point on material 7 will not change due to a lack of contact between material 7 and either the top surface of sample holder 3s or the bottom surface of the associated container 6. In addition, body 8 can be of a high purity metal other than indium, which has been selected only by way of example, the temperature of indium at which the coefficient of thermal conductivity is determined being in the vicinity of 156° C. For other high purity materials, the measurement may be carried out at a different temperature level.

As has been explained above, according to the present invention, widely used DSC apparatus can be utilized for the calculation of the coefficient of thermal conductivity of materials, without any modification of the apparatus. All three constants including thermal diffusibility can also be determined with such DSC apparatus through the combined use of known measurement methods for specific heat and the method according to the invention. Moreover, the coefficient of thermal conductivity of various kinds of solid materials in a form ranging from a thin film to a bulk mass can effectively be determined.

The thermal analysis curves 10 and 11 which are employed for obtaining values for P and Q can be derived with respect to the temperature of sink 1. Alternatively, they can be determined with respect to time, as shown in FIG. 2, particularly when the temperature control program set by apparatus 23 produces a constant rate of temperature increase.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method for measuring the coefficient of thermal conductivity of a solid sample martial having a known thickness and having a thermal resistance, said method comprising:

heating a meltable calibration sample having good thermal conductivity to its melting temperature in a sample station of a thermal analyzer by raising the temperature of the analyzer at a controlled rate and causing heat to flow to the calibration sample through a path having a thermal resistance, said heating step being performed one time with the solid sample material interposed in the path so that heat flows through the path and through the solid sample material, and one time with the solid sample material removed so that heat flows only through the path;

deriving thermal analysis curves each representing a relation between heat flow to the calibration sample and the controlled rate at which the analyzer temperature is raised, over a temperature range which contains the melting temperature of the calibration sample during respective performances of the heating step; and determining the coefficient of thermal conductivity of the solid sample material based on the solid sample material thickness and a characteristic of the thermal analysis curves at the melting temperature of the calibration sample.

2. A method as defined in claim 1 wherein the thermal analyzer is a differential thermal analyzer or a differential scanning calorimeter for observing heat flows to and from a sample in relation to a standard sample which does not undergo a thermal transformation.

3. A method as defined in claim 2 wherein the sample station includes a container made of aluminum, silver, or stainless steel, and the calibration sample is housed within the container.

4. A method as defined in claim 2 wherein the characteristic of the thermal analysis curves which is used to determine the coefficient of thermal conductivity is the maximum absolute value of the slope of each curve at the start of melting of the calibration sample.

5. A method as defined in claim 4 wherein the coefficient k, of thermal conductivity is determined by calculating the equation $$k = \frac{t}{A \cdot B \cdot \left(\frac{1}{P} - \frac{1}{Q}\right)}$$

where: t is the thickness of the sample material;

P is the absolute value of the rate of change of the thermal analysis curve at the melting temperature of the calibration sample and with the solid sample material;

Q is the absolute value of the rate of change of the thermal analysis curve at melting temperature of the calibration sample and without the solid sample material interposed in the path;

A is an effective surface area associated with the solid sample material; and

B is the controlled rate at which the temperature is raised in the sample station.

6. A method for measuring the coefficient of thermal conductivity of a solid sample material having a known thickness and having a thermal resistance, said method comprising:

placing the solid sample material and a meltable calibration sample having good thermal conductivity in a heat flow path having a thermal resistance in a sample station of a thermal analyzer;

heating the meltable calibration sample to its melting temperature in the sample station by raising the temperature of the analyzer at a controlled rate and causing heat to flow to the calibration sample and the solid sample material through the heat flow path;

deriving a thermal analysis curve representing a relation between heat flow to the calibration sample and the controlled rate at which the analyzer temperature is raised, over a temperature range which contains the melting temperature of the calibration sample during the heating step;

comparing the thermal analysis curve derived in said deriving step with a thermal analysis curve produced by raising the temperature of the analyzer at a controlled rate and causing heat to flow to the calibration sample through the heat flow path, with the solid sample material removed from the flow path; and determining the coefficient of thermal conductivity of the solid sample material based on the solid sample material thickness and a characteristic of the thermal analysis curves at the melting temperature of the calibration sample.

* * * * *